United States Patent [19]

Gyurik et al.

[11] 3,956,499

[45] May 11, 1976

[54] METHODS AND COMPOSITIONS FOR PRODUCING POLYPHASIC PARASITICIDE ACTIVITY USING METHYL 5-PROPYLTHIO-2-BENZIMIDAZOLECARBAMATE

[75] Inventors: Robert J. Gyurik, Coatesville; Vassilios J. Theodorides, West Chester, both of Pa.

[73] Assignee: SmithKline Corporation, Philadelphia, Pa.

[22] Filed: Aug. 7, 1975

[21] Appl. No.: 602,704

Related U.S. Application Data

[63] Continuation-in-part of Ser. No. 480,646, June 19, 1974, Pat. No. 3,915,986.

[52] U.S. Cl. .............................................. 424/273
[51] Int. Cl.$^2$...................................... A61K 31/415
[58] Field of Search .................................... 424/273

[56] References Cited
UNITED STATES PATENTS

| | | | |
|---|---|---|---|
| 3,840,550 | 10/1974 | Brenneisen et al. | 424/273 |
| 3,847,932 | 11/1974 | Janiak et al. | 424/273 |

*Primary Examiner*—Sam Rosen
*Attorney, Agent, or Firm*—William H. Edgerton

[57] ABSTRACT

Methyl 5-propylthio-2-benzimidazolecarbamate is the active ingredient for methods and compositions affording enhanced activity against gastrointestinal helminths in commercial or pet animals. It is also active against lungworms, cestodes and flukes in animals.

14 Claims, No Drawings

METHODS AND COMPOSITIONS FOR PRODUCING POLYPHASIC PARASITICIDE ACTIVITY USING METHYL 5-PROPYLTHIO-2-BENZIMIDAZOLECARBAMATE

This application is a continuation-in-part of copending Serial No. 480,646, filed June 19, 1974, now U.S. Patent 3,915,968.

This invention relates to a new compound, methyl 5-propylthio-2-benzimidazolecarbamate, as well as methods and compositions using it as an active ingredient to combat infections of certain parasites in animals.

This compound is included in a large generic class of compounds disclosed in U.S. Pat. No. 3,574,845. See FIG. I at column 1 in which R is hydrogen, R' is lower alkyl, X and X' are oxygen, Y is hydrogen and Z is lower alkyl thio. "Lower alkyl" is defined as having 1 to 8 carbon atoms, column 1, last line. The preferred species of the generic group of U.S. Pat. No. 3,574,845 does not include even lower alkyl thio. The closest compounds in the structure specifically disclosed here is 5-methylthio-2-carboethoxyaminobenzimidazole, column 2, line 67, or the oxy congener, column 3, line 36. The first compound differs from that of this invention by two methylene units at the 5-position and one in the carbalkoxy position, the second by having an oxygen rather than a sulfur.

We have unexpectedly found this new active anthelmintic agent to be extremely active not only against the gastrointestinal parasites as disclosed by the reference patent but also against lungworm infections of animals. These parasites are of the Dictyocaulidae, Metastrongylidae, Prostostrongylidae, and Filaroididae families, especially the genus Dictyocaulus which are prevalent in sheep, cattle and horses. They are particularly resistant to standard anthelmintic agents. Metastrongylus is important in pigs, Protostrongylus in sheep and goats, and Filaroides in cats and dogs. Certain lungworms have been reported to be vectors for the influenza virus in swine.

The following study in sheep demonstrates the unexpected nature of the activity of the propylthio compound of this invention compared with its oxygen congener (oxibendazole) and/or its methylthio congener which are both disclosed in the reference patent.

Thirty-one (31) susceptible lambs were dehelminthized using thiabendazole drench (66 mg./kg.), then levamisole drench (7.5 mg./kg.) to eliminate unwanted nematodes. Fecal counts confirmed the wormfree nature of the test animals which were maintained in clean quarters and fed alfalfa pellets and watered ad libitum. Each lamb was infected orally with filariform larvae as follows:

| Haemonchus | 5000/head for 2 days, |
| Nematodirus | 3500/head for 2 days, |
| Dictyocaulus | 600/head for 2 days. |

The infected larvae were prepared from coprocultures of donor animals carrying monospecific infections of the three parasites.

On the 24th day, egg counts were made using the modified Stoll method to confirm the patency of the infection. Fecal pellets were Baermannized to recover the Dictyocaulus larvae. The infected sheep were divided into control and treated groups. They were sacrificed and processed by standard helminthological procedures to give the following results.

TABLE I

| Lamb No. | Weight Kg. | Worms Recovered | | |
|---|---|---|---|---|
| | | Haemonchus | Nematodirus | Dictyocaulus |
| CONTROL | | | | |
| 519 | 16.0 | | 5100 | 3040 | 102 |
| 536 | 15.9 | | 9850 | 5280 | 297 |
| 522 | 20.6 | | 5140 | 5320 | 281 |
| 538 | 16.2 | | 1700 | 1820 | 70 |
| 516 | 24.1 | | 3300 | 5270 | 138 |
| 512 | 18.9 | 4630 | 5090 | 149 |
| | | Mean 4953 | 4303 | 173 |
| METHYL 5-PROPYLOXY-2-BENZIMIDAZOLECARBAMATE - 15 mg./kg. | | | | |
| 540 | 15.5 | 110 | 2610 | 137 |
| 534 | 21.9 | 0 | 100 | 284 |
| 521 | 23.4 | 220 | 590 | 60 |
| 515 | 19.3 | 10 | 230 | 277 |
| 523 | 13.8 | Died 4/27/74 - no worm recovery. | | |
| | | Mean 85 | 883 | 190 |
| | | % Reduction 98.3 | 79.5 | 0 |
| METHYL 5-METHYLTHIO-2-BENZIMIDAZOLECARBAMATE - 5 mg./kg. | | | | |
| 513 | 22.6 | 3760 | 5350 | 109 |
| 517 | 15.6 | 1100 | 5850 | 400 |
| 541 | 13.6 | 2600 | 240 | 300 |
| | | Mean 2487 | 3813 | 270 |
| | | % Reduction 49.8 | 11.4 | 0 |
| METHYL 5-PROPYLTHIO-2-BENZIMIDAZOLECARBAMATE - 2.5 mg./kg. | | | | |
| 512 | 18.0 | 160 | 760 | 80 |
| 518 | 24.2 | 0 | 80 | 2 |
| 537 | 20.1 | 810 | 0 | 107 |
| 524 | 27.3 | 120 | 10 | 11 |
| 531 | 16.4 | 100 | 720 | 189 |
| 528 | 27.6 | 0 | 10 | 115 |
| | | Mean 198 | 263 | 84 |
| | | % Reduction 96.0 | 93.9 | 51.4 |

TABLE I-continued

| Lamb No. | Weight Kg. | Worms Recovered | | |
|---|---|---|---|---|
| | | Haemonchus | Nematodirus | Dictyocaulus |
| METHYL 5-PROPYLTHIO-2-BENZIMIDAZOLECARBAMATE - 5 mg./kg. | | | | |
| 543 | 20.3 | 140 | 1410 | 63 |
| 535 | 16.8 | 0 | 0 | 58 |
| 539 | 19.1 | 150 | 10 | 12 |
| 520 | 18.7 | 10 | 0 | 21 |
| 514 | 19.5 | 80 | 10 | 0 |
| 533 | 17.0 | 0 | 0 | 19 |
| | Mean | 63 | 238 | 29 |
| | % Reduction | 98.7 | 94.5 | 83.2 |
| METHYL 5-PROPYLTHIO-2-BENZIMIDAZOLECARBAMATE - 10 mg./kg. | | | | |
| 529 | 23.7 | 10 | 30 | 34 |
| 526 | 14.4 | 0 | 0 | 0 |
| 511 | 21.6 | 0 | 0 | 17 |
| 525 | 24.7 | 0 | 0 | 0 |
| 542 | 22.3 | 10 | 0 | 0 |
| | Mean | 4 | 6 | 10 |
| | % Reduction | 99.9 | 99.9 | 94.2 |

The recorded worm recoveries indicate that the propyloxy compound at 15 mg./kg. showed no activity against the lungworm, Dictyocaulus and 98% and 80% efficacy against Haemonchus and Nematodirus, respectively. The methylthio compound at 5 mg./kg. demonstrated very slight activity against the gastrointestinal worms and no activity against the lungworm. The propylthio active ingredient of this invention showed extremely high efficacy against Haemonchus and Nematodirus at all doses. Against lungworm it was active at 51.4% at 2.5 mg./kg.; 83.2% at 5 mg./kg.; and 94.2% at 10 mg./kg.

Earlier studies in lambs drenched with a 10 mg./kg., 5% suspension in carboxymethylcellulose solution gave 100% elimination of Dictyocaulus filaria; a similar drench at 5 mg./kg. against Nematodirus spathiger in sheep gave 99.5% elimination compared to 89% for the standard thiabendazole (50 mg./kg.) and 98% for levamisole (7.5 mg./kg.); a similar drench at 5 mg./kg. in sheep against Haemonchus contortus gave 100% reduction of epg and 99.7% in worm elimination compared to 65.8% and 84.2% for thiabendazole (50 mg./kg.); at 0.05% of diet against the migrating stages of Ascaris suum in mice, mean lung lesions were reduced to 1.5 over infected controls of 2.7 with no deaths in the propylthio treated animals and only three survivors out of ten in the infected controls. In another study four lambs treated with a 10% drench of propyloxy congener of the prior art at 30 mg./kg. gave no effect on Dictyocaulus (lungworm). Details of these tests are available at the request of the Patent Office.

The data show that the active ingredient of this invention affords dual activity against helminths at two different sites, the gastrointestinal tract and the lungs.

The active ingredient, methyl 5-propylthio-2-benzimidazolecarbamate, is prepared by reacting carbomethoxycyanamide with 4-propylthio-o-phenylene diamine or an acid addition salt thereof usually in an aqueous miscible solvent in which the reactants are soluble, such as aqueous acetone, water, pyridine-water, ethanol or mixtures of various water-miscible solvents. The reaction is often run at about room temperature up to the boiling point of the solvent mixture used and if necessary alkali may be added.

As an alternative, the diamine is reacted with cyanogen bromide to give the intermediate, 2-amino-5-propylthiobenzimidazole, which is then reacted with methylchloroformate to form the desired compound. This is the same reaction as above but carried out in two distinct steps.

The following is a specific example of the preparation of the compound of this invention.

A mixture of 6.65 g. of 3-chloro-6-nitroacetanilide, 3.2 ml. of propylmercaptan, 5.6 g. of 50% sodium hydroxide and 100 ml. of water is heated at reflux overnight. The cooled mixture is filtered to give the desired 2-nitro-5-propylthioaniline, m.p. 69.5°–71.5°C. after recrystallization from ethanol then hexane-ether. N.M.R. CDCl$_3$) 40%.

The aniline (2.5 g.) is hydrogenated with 1.9 ml. of concentrated hydrochloric acid, 100 ml. ethanol and 5% palladium-on-charcoal to give 4-propylthio-o-phenylenediamine hydrochloride.

A mixture of 2.5 ml. of 50% sodium hydroxide in 5 ml. of water is added to a mixture of 1.9 g. of cyanamide, 2.2 g. of methylchloroformate, 3.5 ml. of water and 3 ml. of acetone over 45 minutes below 10°C., pH raised to u 6.5. A molar equivalent solution of the diamine in 100 ml. of ethanol is added. The mixture is heated until the easily volatile solvents are expelled, to about 85°C., then maintained at this temperature with some water added for one-half hour. The product, methyl 5-propylthio-2-benzimidazolecarbamate, is separated, washed to give a colorless crystalline solid, m.p. 208°–210°C. N.M.R. and T.L.C. consistent.

The methods of this invention for treating parasitically infected or exposed animals comprise the oral administration of an effective but nontoxic quantity of methyl 5-propylthio-2-benzimidazolecarbamate to said animals. The animals most usually treated are swine, sheep, cattle or horses but any infected commercial or pet animal can be the subject of these new methods. The subject animals may have either gastrointestinal infestations of the type disclosed in U.S. Pat. No. 3,574,845 or preferably lungworm infections. In effect, the new methods give a dual activity against gastrointestinal and lung parasites at the same dose levels.

The administration may be by any of the commonly used oral veterinary methods for anthelmintic treatment, such as by bolus, tablet, drench, top dressing, etc. Animals of low weight are treated with unit doses ranging no higher than a few milligrams; whereas animals of high body weight, such as ruminants as sheep or cattle, require proportionately larger unit doses ranging up to several grams. Preferably, a single dose is administered from 1-5 times or preferably once or twice to clear the animals or sometimes daily for each animal species.

The amount of ingredient administered will therefore depend on the weight of the host, but will usually be between about 1 mg./kg. and 100 mg./kg., preferably about 5-15 mg./kg., of body weight per dose.

The method may be applied as a curative to infected animals or in somewhat lower doses prophylactically to animals potentially exposed to internal parasites. Most advantageously the methods of this invention comprise the oral administration for curative or prophylactic purposes to animals infected with or exposed to a lungworm, for example a Dictyocaulidae, preferably in sheep, cattle or horses.

In addition to lungworm infection as noted below, the 5-propylthiobenzimidazolecarbamate of this invention has most useful general anthelmintic properties, that is, broad spectrum activity against gastrointestinal parasites of warm blooded animals, including both mature and immature parasitic forms. In particular, this compound has high activity against various helminthic infections of the intestinal tract of economically important animals, coupled with low systemic toxicity to the host animal.

For example, the disclosed compounds are generally effective in clearing mice of worm infections for laboratory purposes, among others: *Syphacia obvelata* and *Aspicularis tetraptera* (mouse pinworm), *Nematospiroides dubius* (mouse hookworm), and the migratory stages of *Ascaris suum*.

Other susceptible helminths include *Toxocara canis*, found in naturally infested dogs. Also, parasitic to this host are *Ancylostoma canium*, *Trichuris vulpis* (whipworm), and *Physalaptera spp*.

These compounds are efficacious against parasites of pigs, such as the migratory stages of *Ascaris suum*, thus preventing the development of verminous pneumonia.

Among the gastrointestinal parasites in sheep and cattle which are susceptible are *Haemonchus contortus*, *Ostertagia spp.*, *Trichostrongylus spp.*, *Nematodirus spp.*, *Trichuris ovis*, *Cooperia spp.*, and *Strongyloides papillosus, Bunostomum spp., Chabertia sp.* and *Oesophagostomum spp.*, are other important parasites of sheep.

In practice, the active propylthio compound is usually formulated with a nontoxic animal veterinary or feed carrier therefor to give the anthelmintic compositions of this invention. The carrier may be a standard animal feed composition based on a feed carrier or an orally ingestible container for the active ingredient, for example, a hard or soft gelatin capsule; or it may be a pharmaceutically acceptable diluent or excipient of the kind normally used in the production of medicaments, ready for use, for example maize starch, terra alba, lactose, sucrose, calcium phosphate, gelatin, talcum stearic acid, magnesium stearate, dextrin, agar, pectin or acacia.

Exemplary of liquid carriers are peanut oil, olive oil, sesame oil, and water. Similarly, the carrier or diluent may include a time delay material, such as glyceryl monostearate or glyceryl distearate alone or with a wax.

A wide variety of pharmaceutical or veterinary forms can be employed. Thus, if a solid carrier is used, the preparation can be tableted, placed in a hard gelatin capsule, compounded in the form of a salt block, as a powder for drench or gavage use, whole feed or top dressing mixed with standard animal feed carriers as noted in U.S. Pat. No. 3,812,255. The amount of solid veterinary carrier will vary widely but preferably will be from about 25 mg. to about 3 gm. for the nonfeed carriers. If a liquid carrier is used, the preparation may be in a soft gelatin capsule, in an ampule or in liquid suspension.

The compositions are most often made up in a form suitable for oral administration and may therefore take the form of a liquid, for example, an emulsion or a solution or suspension in water, oil, such as arachis oil, or other liquid.

The compositions are advantageously made up in a dosage unit form adapted for the desired mode of administration. Thus for the preferred oral administration, the dosage unit may take the form of a suspension, top dressing, tablet, packaged powder, bolus, or encapsulated powder. The quantity of active ingredient in each dosage unit will be such that one or more units are required for each therapeutic administration.

Where tableting is used, the resulting tablets may then be coated with methyl methacrylate to form an enteric coating, i.e., a coating which is substantially insoluble in gastric secretion but substantially soluble in intestinal fluids.

The compositions thusly prepared are administered, usually orally, to an infected or susceptible host from 1-5 times daily for curative or prophylactic anthelmintic activity.

The following examples illustrate specific aspects of the invention which may be employed in formulating the compositions of the invention but are not considered to limit the scope of the invention described herebefore.

EXAMPLE 1

| Typical Cattle Bolus | |
|---|---|
| Methyl 5-propylthio-2-benzimidazole-carbamate | 0.15 grams |
| Calcium Phosphate | 2.5 grams |
| Maize Starch | 0.54 grams |
| Talcum | 0.14 grams |
| Gum Arabic | 0.15 grams |
| Magnesium Stearate | 0.5 grams |

The calcium phosphate and the anthelmintic compounds are thoroughly mixed, and the mixture reduced to a particle size finer than 60 mesh. About one-half of the starch is added, as an aqueous paste, and the resulting mixture granulated. The granules are passed through a 10 mesh screen and dried at 110°–130°F. for about eight hours. The dried materials are then passed through a No. 16 mesh screen. The guar gum and the balance of the starch are added and the mixture thoroughly blended. Finally, the remainder of the ingredients are added and the entire mass thoroughly mixed and compressed into a bolus. The magnesium stearate, talcum and gum acacia are of a particle size to pass a No. 10 mesh screen.

EXAMPLE 2

| Sheep Drench | Parts by Weight |
|---|---|
| Methyl 5-propylthio-2-benzimidazole-carbamate | 60 |
| Terra Alba English | 35.5 |
| Tragacanth, U.S.P. | 3.0 |
| Sodium Lauryl Sulfate | 1.5 |
| Water | |

The above solid components are thoroughly mixed, giving a water dispersable powder. This powder can be directly admixed with water in concentrations on the order of 10.5 g. of powder to 5 cc. of water.

EXAMPLE 3

| Sheep Drench | |
|---|---|
| Methyl 5-propylthio-2-benzimidazole-carbamate | 2 grams |
| 0.1N HCl Solution | Quantum sufficient to make 1 liter. |

The description of this invention has been limited to a single compound, methyl 5-propylthio-2-benzimidazolecarbamate. The novel part of the structure of this subject compound which gives enhanced anthelmintic activity against gastrointestinal helminths and unique activity against lungworms is the propylthio group. Other carbamate esters may be substituted in the general invention as known to the art, for example lower alkyl of from 1–8 carbon atoms such as methyl, ethyl, propionyl, furyl, benzyl, etc. Other acyl groups may be substituted on the 2-amino, for example lower alkanoyl such as acetyl, propionyl, benzoyl, furoyl, etc. Also further N-acylation or alkylation, i.e., at one or both of the ring nitrogens at position 1 or 3, may be carried out but with little additional advantage.

The methods and compositions of this invention using methyl 5-propylthio-2-benzimidazolecarbamate are also applicable to ruminants especially cattle and sheep infected or exposed to tapeworms (cestodes). For example, at 10 and 15 mg./kg. complete control of Moniezia and Avitellina in sheep was achieved. In sheep at 50 mg./kg. complete elimination of flukes was achieved after artificial infection with 300 metacercaraie of Fasciola hepatica. In 10 lambs an oral drench containing 20 mg./kg. gave 100% efficacy against adult Fasciola hepatica. At 10 mg./kg., 99% efficacy was achieved. An oral dose range of from about 5–50 mg./kg. has, therefore, shown to be very effective against flukes.

We claim:

1. The method of producing anthelmintic activity in animals infected with or susceptible to helminthic infections comprising administering orally to said animals an anthelmintically effective but nontoxic quantity of methyl 5-propylthio-2-benzimidazolecarbamate.

2. The method of claim 1 in which the helminths are Nematodes, lungworms, cestodes or flukes.

3. The method of claim 1 in which the quantity is chosen from the range of about 1–100 mg./kg. per dose based on the animal weight.

4. The method of claim 1 in which the quantity is chosen from the range of about 5–15 mg./kg. per dose based on the animal weight.

5. The method of claim 4 in which the helminth is a lungworm, Nematode or cestode.

6. The method of claim 1 in which the helminth is a Dictyocaulus and the animal host is sheep, cattle or horses.

7. The method of claim 6 in which the unit dose is chosen from the range of about 5–15 mg./kg. based on the animal weight.

8. The method of claim 1 in which the helminths are present in both the gastrointestinal tract and in the lungs.

9. The anthelmintic composition for animals having activity against Nematodes, lungworms, cestodes or flukes comprising a veterinary or feed carrier and dispersed uniformly therein a quantity of methyl 5-propylthio-2-benzimidazolecarbamate which is anthelmintically effective but nontoxic to the host animal, said quantity being chosen from the range of about 1–100 mg./kg. per dosage unit based on body weight.

10. The composition of claim 9 in which the range is about 5–15 mg./kg.

11. The composition of claim 9 in which the helminth is lungworm.

12. The composition of claim 9 in which the composition is for ruminants and the helminth is lungworm.

13. The composition of claim 9 in which the helminth is cestode.

14. The composition of claim 9 in which the helminth is fluke.

* * * * *